United States Patent
Pilch et al.

(10) Patent No.: US 9,149,661 B2
(45) Date of Patent: Oct. 6, 2015

(54) ANTI-EROSION TOOTHPASTE COMPOSITION

(75) Inventors: Shira Pilch, Highland Park, NJ (US); James Masters, Ringoes, NJ (US); Richard Sullivan, Atlantic Highlands, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/515,823

(22) PCT Filed: Dec. 17, 2010

(86) PCT No.: PCT/US2010/060970
§ 371 (c)(1),
(2), (4) Date: Jun. 14, 2012

(87) PCT Pub. No.: WO2011/084673
PCT Pub. Date: Jul. 14, 2011

(65) Prior Publication Data
US 2012/0251466 A1    Oct. 4, 2012

Related U.S. Application Data

(60) Provisional application No. 61/287,292, filed on Dec. 17, 2009.

(51) Int. Cl.
| A61Q 11/00 | (2006.01) |
| A61K 8/24 | (2006.01) |
| A61K 8/20 | (2006.01) |
| A61K 8/21 | (2006.01) |

(52) U.S. Cl.
CPC . *A61Q 11/00* (2013.01); *A61K 8/21* (2013.01); *A61K 8/24* (2013.01); *A61K 2800/52* (2013.01)

(58) Field of Classification Search
USPC ............. 424/52, 49, 57, 401; 433/215, 216, 433/217.1
See application file for complete search history.

(56) References Cited

U.S. PATENT DOCUMENTS

| 3,538,230 A | 11/1970 | Pader et al. |
| 3,956,480 A | 5/1976 | Dichter et al. |
| 3,966,863 A | 6/1976 | Forward et al. |
| 3,980,767 A | 9/1976 | Chown et al. |
| 3,996,863 A | 12/1976 | Osborn |
| 4,110,083 A | 8/1978 | Benedict |
| 4,138,477 A | 2/1979 | Gaffar |
| 4,138,914 A | 2/1979 | Reeder |
| 4,198,394 A | 4/1980 | Faunce |
| 4,314,990 A | 2/1982 | Denny, Jr. et al. |
| 4,328,205 A | 5/1982 | Taylor |
| 4,358,437 A | 11/1982 | Duke |
| 4,373,036 A | 2/1983 | Chang et al. |
| 4,485,090 A | 11/1984 | Chang |
| 4,521,551 A | 6/1985 | Chang et al. |
| 4,532,124 A | 7/1985 | Pearce |
| 4,634,589 A | 1/1987 | Scheller |
| 4,853,367 A | 8/1989 | Henzel et al. |
| 4,992,258 A | 2/1991 | Mason |
| 5,028,413 A | 7/1991 | Bianchi et al. |
| 5,032,178 A | 7/1991 | Cornell |
| 5,188,821 A | 2/1993 | Gaffar |
| 5,192,531 A | 3/1993 | Gaffar et al. |
| 5,240,697 A | 8/1993 | Norfleet et al. |
| 5,310,543 A | 5/1994 | Dawson |
| 5,352,439 A | 10/1994 | Norfleet et al. |
| 5,354,550 A | 10/1994 | Collins et al. |
| 5,505,933 A | 4/1996 | Norfleet et al. |
| 5,603,922 A | 2/1997 | Winston et al. |
| 5,605,677 A | 2/1997 | Schumann et al. |
| 5,624,652 A | 4/1997 | Aldcroft et al. |
| 5,645,853 A | 7/1997 | Winston et al. |
| 5,723,105 A | 3/1998 | Viscio et al. |
| 5,833,954 A * | 11/1998 | Chow et al. ................ 424/49 |
| 5,833,957 A | 11/1998 | Winston et al. |
| 5,876,701 A | 3/1999 | Wong et al. |
| 5,939,051 A | 8/1999 | Santalucia et al. |
| 6,036,944 A | 3/2000 | Winston et al. |
| 6,117,415 A | 9/2000 | Schwarz |
| 6,214,321 B1 | 4/2001 | Lee et al. |
| 6,217,851 B1 | 4/2001 | Kleinberg et al. |
| 6,241,972 B1 | 6/2001 | Herms et al. |
| 6,248,310 B1 | 6/2001 | Lee et al. |
| 6,294,163 B1 | 9/2001 | Dhal et al. |
| 6,447,756 B1 | 9/2002 | Dixit et al. |
| 6,524,558 B2 | 2/2003 | Kleinberg et al. |
| 6,790,460 B2 | 9/2004 | Shefer et al. |
| 6,936,640 B2 | 8/2005 | McQueen et al. |
| 6,953,817 B2 | 10/2005 | Fisher et al. |
| 7,018,625 B2 | 3/2006 | Ulmer et al. |

(Continued)

FOREIGN PATENT DOCUMENTS

| CN | 1411364 | 4/2003 |
| EP | 0102200 | 3/1984 |

(Continued)

OTHER PUBLICATIONS

Cold Spring Harbor Protocols, Recipe, Sodium Phosphate, pp. 1 and 2, 2006.*
Waszkiel et al., "Efficacy of Fluoride varnishes in the Prophylaxis of Dental Erosion", Research Report Fluoride, 39(1), 49-52, Jan.-Mar. 2006.*
Acevedo et al., 2005, "The Inhibitory Effect of an Arginine Bicarbonate/Calcium Carbonate (CaviStat®)-Containing Dentifrice on the Development of Dental Caries in Venezuelan School Children," J. Clin. Dent. 16:63-70.
Amaechi et al., 2005, "Dental Erosion: Possible Approaches to Prevention and Control," J. Dentistry 33(3):243-252.
Anonymous, 2007, "Sensodyne Pronamel Toothpaste Sensodyne Enamel-Pro Toothpaste," Safeguarding Public Health, MHRA.
Ariely et al., 1966, "Synthesis of Poly-L-Arginine," Biopolymers 4(1):91-96.
Cunin et al., 1986, "Biosynthesis and Metabolism of Arginine in Bacteria," Microbiological Reviews, 50(3):314-352.

(Continued)

*Primary Examiner* — Lezah Roberts

(57) ABSTRACT

Disclosed herein are oral care compositions comprising a fluoride ion source and phosphate salts, and methods of making and using the same.

2 Claims, No Drawings

(56) References Cited

U.S. PATENT DOCUMENTS

| | | |
|---|---|---|
| 7,402,416 B2 | 7/2008 | Szeles et al. |
| 7,435,409 B2 | 10/2008 | Nelson et al. |
| 2002/0037258 A1 | 3/2002 | Dodd et al. |
| 2003/0026768 A1 | 2/2003 | Yu et al. |
| 2004/0126335 A1 | 7/2004 | Faller et al. |
| 2004/0241108 A1 | 12/2004 | Stanier et al. |
| 2005/0129628 A1 | 6/2005 | Stanier et al. |
| 2005/0186288 A1 | 8/2005 | Chiou et al. |
| 2005/0196358 A1 | 9/2005 | Georgiades et al. |
| 2005/0281757 A1 | 12/2005 | Ibrahim et al. |
| 2006/0008423 A1 | 1/2006 | Araya et al. |
| 2006/0024246 A1 | 2/2006 | Maitra et al. |
| 2006/0039957 A1 | 2/2006 | Krumme |
| 2006/0045851 A1 | 3/2006 | Fitzgerald et al. |
| 2006/0251737 A1 | 11/2006 | Dutra Zanotto et al. |
| 2007/0014741 A1 | 1/2007 | Chiu |
| 2007/0104660 A1 | 5/2007 | Miksa et al. |
| 2008/0226566 A1 | 9/2008 | Poth et al. |
| 2008/0267891 A1 | 10/2008 | Zaidel et al. |
| 2008/0268001 A1 | 10/2008 | Zaidel et al. |
| 2009/0068259 A1 | 3/2009 | Pilch et al. |

FOREIGN PATENT DOCUMENTS

| | | |
|---|---|---|
| EP | 0467548 | 1/1992 |
| EP | 0480812 | 4/1992 |
| EP | 0845976 | 6/1998 |
| EP | 1260482 | 11/2002 |
| GB | 1598233 | 9/1981 |
| JP | S4969848 | 7/1974 |
| JP | S49109543 | 10/1974 |
| JP | S61130213 | 6/1986 |
| JP | 2001-247310 A | 12/2001 |
| RU | 2085184 | 7/1997 |
| WO | WO 93/07851 | 4/1993 |
| WO | WO 00/16712 | 3/2000 |
| WO | WO 01/70178 | 9/2001 |
| WO | WO 2004/032674 | 4/2004 |
| WO | WO 2005/063185 | 7/2005 |
| WO | WO 2007/051546 | 5/2007 |
| WO | WO 2009/009814 | 1/2009 |
| WO | WO 2009/032404 | 3/2009 |
| WO | WO 2011/094499 | 8/2011 |
| WO | WO 2011/094505 | 8/2011 |

OTHER PUBLICATIONS

Hefferren, 1976, "A Laboratory Method for Assessment of Dentifrice Abrasivity," J. Dent. Res. 55(4):563-573.

International Search Report and Written Opinion in International Application No. PCT/US08/061925, mailed Feb. 5, 2010.

International Search Report and Written Opinion in International Application No. PCT/US09/044349, mailed Dec. 8, 2009.

International Search Report and Written Opinion in International Application No. PCT/US10/021582, mailed Aug. 9, 2011.

International Sarch Report and Written Opinion in International Application No. PCT/US10/060970, mailed May 31, 2012.

Jal et al., 2004, "Chemical modification of silica surface by immobilization of functional groups for extractive concentration of metal ions," Talanta 62(5):1005-1028.

Johnson et al., 2006, "Oral Health and General Health," Advances in Dental Research 19:118-121.

McConnell et al., 2010, "Bacterial plaque retention on oral hard materials: Effect of surface roughness, surface composition, and physisorbed polycarboxylate," J. Biomedical Materials Research Part A 92(4):1518-1527.

Pashley et al., 1984, "Effects of Desensitizing Dentifrices in vitro," J. Periodontology 55(9):522-525.

Pashley et al., 1993, "The Effects of Outward Forced Convective Flow on Inward Diffusion in Human Dentine in vitro," Arch. Oral Biol. 38(7):577-582.

Pashley et al., 2002, "The Effects of Outward Forced Convective Flow on Inward Diffusion of Potassium across Human Dentin," American J. of Dentistry, Medline Database Accession No. NLM12572645, Abstract.

Sakai et al., 2003, "Anion-Mediated Transfer of Polyarginine Across Liquid and Bilayer Membranes," J. Am. Chem. Soc. 125(47):14348-14356.

Stober et al., 1968, "Controlled Growth of Monodisperse Silica Spheres in the Micron Size Range," J. Colloid and Interface Science 26:62-69.

Zhang et al., 1998, "The Effects of Pain-Free Desensitizer on Dentine Permability and Tubule Occlusion over Time, in vitro," J. Clinical Periodontology 25(11 Pt. 1):884-891.

Borovsky, 2004, "Therapeutic Dentistry Textbook for Medical Students," Meditsinskoe Informatsionnoe Agentstvo, pp. 181-183 with English translation.

* cited by examiner

ANTI-EROSION TOOTHPASTE COMPOSITION

CROSS REFERENCE TO RELATED APPLICATIONS

This application is a national stage entry under 35 U.S.C. §371 of International Patent Application No. PCT/US2010/060970, filed 17 Dec. 2010, which claims priority to U.S. Provisional Patent Application Ser. No. 61/287,292, filed on 17 Dec. 2009, which is incorporated herein by reference.

FIELD

An anti-erosion oral care composition that reduces acid erosion of tooth enamel. More particularly, toothpaste compositions containing a fluoride ion source and phosphate salts that provide superior anti-erosion benefits.

BACKGROUND

The erosion of dental enamel can lead to pain, discoloration, mechanical failure, and greater susceptibility to dental carries. Chemical erosion of tooth enamel may arise from the presence of acid in the oral cavity. Saliva constituents, mainly proteins and minerals, along with the pellicle are integral in protecting against an erosive challenge. The minerals and proteins in saliva help provide a chemical barrier to slow down or shift the complex dynamic equilibria of hard tissue demineralization, while the pellicle will provide a diffusion barrier to accomplish the same process. Further, the pH value and the presence of species such as phosphate and fluoride help determine the degree of saturation with respect to tooth mineral composition and the driving force for dissolution.

One of the many purposes that oral care compositions may serve is to help control pH in the oral cavity. A common strategy when attempting to control oral pH is to include an alkaline agent in the formulation of an oral care composition. The alkaline agent reacts with acid to neutralize the acid, forming water and a salt. This process raises the pH in the oral cavity. The alkaline agent has the capacity to neutralize an equivalent amount of acid. Limited amounts of alkaline agent may be integrated into an oral care composition. An alternative to an alkaline agent is the use of a buffer system. Buffer systems may be designed to stay within a particular pH range based on their composition. Buffer systems also may be safely included in oral care compositions at a higher loading than a pure alkaline agent. While the prior art recognizes the inclusion of buffer systems in oral care compositions for the purpose of maintaining pH, these buffer systems do not have high enough buffer capacity to protect against acid based enamel erosion.

SUMMARY

A composition and method for the prevention of dental erosion using a multi-component oral care composition comprising an orally acceptable vehicle, a fluoride salt, and a phosphate buffer. A composition that comprises an orally acceptable vehicle, a fluoride salt, and a phosphate buffer comprising monobasic sodium phosphate and dibasic sodium phosphate in a ratio from 12:88 to 18:82, preferably at a weight percentage of 3.5 to 4.5% of the final composition. A method of using a composition that comprises an orally acceptable vehicle, a fluoride salt, and a phosphate buffer comprising monobasic sodium phosphate and dibasic sodium phosphate in a ratio from 12:88 to 18:82, preferably at a weight percentage of 3.5 to 4.5% of the final composition, to reduce acid erosion of tooth enamel. The composition and method protects tooth enamel from erosion by providing a composition with a high buffer capacity that neutralizes oral acid, decreasing acid induced enamel erosion.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

The oral care compositions of the various embodiments preferably are in the form of a dentifrice. The term "dentifrice" as used throughout this description, denotes a paste, gel, or liquid formulation. The dentifrice may be in any desired form, such as deep striped, surface striped, multilayered, having a gel surround the paste, or any combinations thereof.

The expressions "carrier" or "aqueous carrier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

To prepare an anti-erosive oral care composition, a phosphate buffer and a fluoride source preferably are incorporated into an orally acceptable vehicle.

Phosphate buffers usually are combinations of phosphate salts that serve to resist a change of pH upon addition of an acid to a solution. (See P J Niebergall, "Ionic Solutions and Electrolytic Equilibria" in Remington: The Science and Practice of Pharmacy, $20^{th}$ ed. A R Gennaro ed. 2000) Non-limiting examples of phosphate salts that may be used in combination to form a phosphate buffer include soluble phosphates of the formula $XH_2PO_4$ (monobasic phosphate) or $X_2HPO_4$ (dibasic phosphate) where X may be sodium or potassium. The ratio of the monobasic phosphate and dibasic phosphate can be from 12:88 to 18:82, preferably from 14:86 to 18:82, most preferably 16:84. The weight percentage of the phosphate buffer preferably is the combination of the individual weight percentages of the buffer components. The preferred weight percentage of the phosphate buffer in the final composition is from 3.5 to 4.5%, most preferably 3.75%.

Fluoride ion releasing salts may be incorporated in the orally acceptable vehicle and typically are characterized by their ability to release fluoride ions in water. It is preferable to employ a water soluble fluoride salt providing about 1000 to about 9000 ppm of fluoride ion, and preferably about 2500 to about 8800 ppm of fluoride ion. Suitable examples of fluoride ion releasing salts include water soluble inorganic metal salts, for example, sodium fluoride, potassium fluoride, sodium monofluorophosphate, stannous fluoride and sodium fluorosilicate. Sodium fluoride, sodium monofluorophosphate and stannous fluoride are preferred fluoride ion releasing salts.

The phrase "orally acceptable vehicle" means any dentifrice, toothpaste, mouthwash, lozenge, or troche which may contain any single or combination of the following components: a solvent, an alkaline agent, a humectant, a thickener, a surfactant, an abrasive, an anti-calculus agent, a colorant, a flavoring agent, a dye, a potassium containing salt, and an anti-bacterial agent.

An alkaline agent such as an alkali metal compound including sodium hydroxide, potassium hydroxide, sodium bicarbonate, sodium carbonate, N-sodium silicate (a 3.22 weight ratio of sodium silicate in 34.6% water available from PQ Corporation) can be incorporated in the orally acceptable vehicle in amounts in the range of about 0.5 to about 15% by weight, preferably about 1.0 to about 8% by weight and most preferably at about 1.0 to about 5.0% by weight of the composition. Mixtures of the above alkali metal compounds may also be used. Sodium hydroxide is the preferred alkaline agent.

A humectant used in the preparation of the orally acceptable vehicle is generally a mixture of humectants, such as glycerol, sorbitol and a polyethylene glycol of molecular weight in the range of 200 to 1000, but other mixtures of humectants and single humectants may also be employed. The humectant content preferably is in the range about of 10% to about 50% by weight and preferably about 20 to about 40% by weight of the dentifrice component. The water content can be in the range of about 20 to about 50% by weight and preferably about 30 to about 40% by weight.

Thickeners used in the preparation of the orally acceptable vehicle include organic and inorganic thickeners. Inorganic thickeners which may be included in the orally acceptable vehicle include amorphous silicas such as Zeodent 165 available from Huber Corporation, and Sylox 15 from W. R. Grace. Organic thickeners of natural and synthetic gums and colloids may also be used to prepare the dentifrice components. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. An inorganic thickener may be incorporated in the orally acceptable vehicle at a concentration of 0.5 to 5% by weight and preferably 1 to 3% by weight. The organic thickener may be incorporated in the compositions at a concentration of 0.1 to 3% by weight and preferably 0.4 to 1.5% by weight.

Surfactants may be incorporated in the orally acceptable vehicle to provide foaming properties. The surfactant is preferably anionic or nonionic in nature. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate. The surfactant agent is generally present in the orally acceptable vehicle compositions at a concentration of 0.5 to 10.0% by weight and preferably 1.0 to 5.0% by weight.

Abrasives may be incorporated in the orally acceptable vehicle and preferred abrasives are siliceous materials, such as silica. A preferred silica is a precipitated amorphous hydrated silica, such as Sorbosil AC-35, marketed by Crosfield Chemicals, or Zeodent 115 from Huber Company but other abrasives may also be employed, including hydroxyapatite, sodiummetaphosphate, potassium metaphosphate, tricalcium phosphate, calcium phosphate dihydrate, anhydrous dicalciumphosphate, calcium pyrophosphate, magnesium orthophosphate, trimagnesium phosphate, calcium carbonate, sodium bicarbonate, alumina trihydrate, aluminum silicate, calcined alumina, titania, and bentonite. The concentration of abrasive in the toothpaste compositions will normally be in the range of from 5 to 40% by weight and preferably 10 to 25% by weight.

The source of desensitizing potassium ion is generally a water soluble potassium salt including potassium nitrate, potassium citrate, potassium chloride, potassium bicarbonate and potassium oxalate with potassium nitrate being preferred. The potassium salt is generally incorporated in one or more of the dentifrice components at a concentration of 1 to 20% by weight and preferably 3 to 10% by weight.

Pyrophosphate salts having anticalculus efficacy useful in the practice include water soluble salts such as dialkali or tetraalkali metal pyrophosphate saltssuch as $Na_4P_2O_7$ (TSPP), $K_4P_2O_7$, $Na_2P_2O_7$, $Na_2H_2P_2O_7$ and $K_2H_2P_2O_7$. Polyphosphate salts include the water soluble alkali metal tripolyphosphates such as sodium tripolyphosphate and potassium tripolyphosphate. The pyrophosphate salts are incorporated in the dentifrice composition at a concentration of 0.5 to 2.0% by weight, and preferably 1.5 to 2% by weight and the polyphosphate salts are incorporated in the dentifrice composition at a concentration of 1.0 to 7.0% by weight.

Colorants such as pigments and dyes may be used in the practice. Pigments include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5-1000 microns, preferably 250-500 microns, and are present at a concentration of 0.5 to 3% by weight.

Dyes used are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphto-6-monosulfonate), FD&C Green No. 3 (disodium slat of 4-{[4-(N-ethyl-p-sulfobenzyno)-phenyl]-(4-hydroxy-2-sulfoniumphenyl) mewthylene}-[1-(N-ethyl-N-p-sulfobenzyl)-G)-3, 5cyclohexadienimine], FD&C Blue No. 1 (disodium salt of dibenzyldiethyldiaminotriphenylcarbinol trisulfonic acid of indigo tin) and mixtures thereof in various proportions. The concentration of the dye for the most effective result is present in the dentifrice composition in an amount from 0.0005 percent to 2 percent of the total weight.

Any suitable flavoring or sweetening material may also be incorporated in the dentifrice composition. Examples of suitable flavoring constituents are flavoring oils, e.g., oils of spearmint, peppermint, wintergreen, sassafras, clove, sage, eucalyptus, marjoram, cinnamon lemon, and orange, and methyl salicylate. Suitable sweetening agents include sucrose, lactose, maltose, sorbitol, xylitol, sodium cyclamate, perillatine, and sodium saccharin. Suitably, flavor and sweetening agents may together comprise from 0.01% to 5% or more of the preparations.

Antibacterial agents are non-cationic antibacterial agents based on phenolic and bisphenolic compounds, halogenated diphenyl ethers such as Triclosan, benzoate esters and carbanilides as well as cationic antibacterial agents such as chlorhexidine digluconate. Such antibacterial agents can be present in quantities of from about 0.03 to about 1% by weight of the composition.

When noncationic antibacterial agents or antibacterial agents are included in any of the dentifrice components, there is also preferably included from about 0.05 to about 5% of an agent that enhances the delivery and retention of the agents to, and retention thereof on oral surfaces. Such agents useful are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g. AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to about 3% by weight.

To prepare the compositions described herein, the flavorants and sweeteners, as well as fluoride source, polyphosphates as anti-calculus ingredients, and the like (including, for example, saccharin, sodium fluoride, potassium nitrate, sodium phosphate monobasic, sodium phosphate dibasic), are dissolved in water as part 1 of the composition. The humectants, for example, propylene glycol, and polyethylene glycol ingredients, preferably are dispersed with any organic thickeners, such as carboxymethyl cellulose and/or Xanthan, and pigments such as titanium dioxide as part 2 of the composition. It is preferred then to add additional humectants, such as sorbitol to part 2 of the composition and mix until a homogeneous slurry is formed. Parts 1 and 2 then can be added to one another, and the mixture mixed until a smooth gel is formed. The resulting gel then preferably is transferred to a vacuum mixer, abrasives such as silica can be added to the gel tank, and then mixed for 10-20 minutes at high speed under a vacuum. Surfactants (e.g., sodium lauryl sulfate) and additional flavors can be added to the vacuum tank and the ingredients mixed for an additional 5-10 minutes under vacuum. The resultant product is a homogeneous, semi-solid, extrudable paste product.

The preparation of dentifrice compositions is well known in the art. U.S. Pat. Nos. 3,996,863, 3,980,767, 4,328,205, and 4,358,437 disclose toothpastes and methods of production thereof which may be utilized for the production of the dentifrices.

The invention can be further described with reference to the following examples. The examples are merely illustrative and do not in any way limit the scope of the invention as described and claimed.

EXAMPLES

Example 1

Toothpaste Formulation

An oral care composition of the present invention in the form of a toothpaste was prepared (Toothpaste X). The composition of this oral care composition is listed in Table 1 below.

TABLE 1

Toothpaste X

| Ingredient | % wt/wt |
| --- | --- |
| Sorbitol | 29.4 |
| Glycerin | 20 |
| Water | 18 |
| Potassium Nitrate | 5.17 |
| Sodium Phosphate Monobasic | 0.25 |
| Sodium Phosphate Dibasic | 3.5 |
| Polyethylene Glycol 600 | 3 |
| Silica | 16 |
| Sodium Lauryl Sulfate (SLS) | 1.2 |
| NaF | 0.32 |
| Flavor | 1 |
| Tetrasodium Pyrophosphate | 0.5 |
| Carboxy methyl cellulose (CMC) | 0.7 |
| Sodium Saccharin | 0.3 |
| Xanthan Gum | 0.2 |
| Titania | 0.5 |

Toothpaste X was prepared as follows:

Dissolve Saccharin, Sodium Fluoride, Potassium Nitrate, Sodium Phosphate Monobasic, Sodium Phosphate Dibasic in water as part 1.

Disperse Tetrasodium Pyrophosphate, the organic thickeners (CMC and Xanthan), and Titanium Dioxide in Polyethylene Glycol 600 and Glycerine as part 2

Add Sorbitol to part 2, mix until homogenous slurry is formed

Add part 1 to part 2 and sorbitol mixture, mix until smooth gel is formed

The resulting gel was transferred to a vacuum mixer

Silica was then added to the gel tank and mixed for 10-20 minutes at high speed under a vacuum The Sodium Lauryl Sulfate and flavor were then added to the vacuum tank and mixed for 5-10 minutes under vacuum A pH titration experiment was designed to illustrate the buffering effect of toothpaste X vs. a fluoride containing toothpaste and a commercial anti-erosion toothpaste (ProNamel®). In this experiment, toothpaste was diluted with water at a 1:2 ratio. The toothpaste slurry was titrated with 0.1 M HCl solution.

TABLE 2

Grams of Acid Required to Lower the pH of a Toothpaste Slurry to 6

| | g, acid/g, TP slurry |
| --- | --- |
| Toothpaste X | 0.71 |
| Regular Fluoride control | 0.08 |
| ProNamel ® (EU) | 0.03 |
| ProNamel ® (US) | 0.05 |

Table 1 shows the amount of acid solution needed to lower the pH of 1 gram of toothpaste slurry to pH 6. The results show that the buffering capacity of toothpaste X is about 9 times that of a regular fluoride containing toothpaste, indicating that a greater degree of acid neutralization would be expected with the use of toothpaste X.

The ability of toothpaste X to protect against acid induced enamel erosion was tested in an acid challenge test. In this experiment, polished enamel was treated with 5% citric acid for 10 seconds. The acid etched enamel was then exposed to a toothpaste slurry (1:1 toothpaste:water) for 5 minutes. The treated surface was quantified using profilometry before acid treatment, after acid treatment, and after toothpaste treatment. Table 3 shows the decrease in wear effected by three toothpastes. The results indicate that the phosphate buffer system of the present invention provided the largest decrease in wear of the three tested compositions.

TABLE 3

The anti-erosion effect of toothpastes

| | Decrease in Wear ($\mu m^2$) |
|---|---|
| Control (1450 ppm F) | 10.37 |
| Phosphate Formula (Invention) | 29.07 |
| ProNamel ® | 10.68 |

The pH titration and profilometry results provide evidence that the combination of a unique high capacity phosphate buffer with a fluoride source in the oral care composition of the present invention provides the unexpected result of significant improvement in the decrease in erosion of tooth enamel when exposed to acid.

What is claimed is:

1. A single component anti-erosion toothpaste comprising:
a) an orally acceptable vehicle;
b) a fluoride ion source; and
c) a phosphate buffer comprising monobasic sodium phosphate and dibasic sodium phosphate in a ratio of 16:84, wherein the single component anti-erosion tooth paste comprises 3.75% by weight of the combined weight of monobasic sodium phosphate and dibasic sodium phosphate.

2. A method of reducing tooth erosion comprising:
a) delivering to the oral cavity a composition comprising:
i) an orally acceptable vehicle;
ii) a fluoride ion source; and
iii) a phosphate buffer comprising monobasic sodium phosphate and dibasic sodium phosphate in a ratio of 16:84, wherein the single component anti-erosion tooth paste comprises 3.75% by weight of the combined weight of monobasic sodium phosphate and dibasic sodium phosphate.

* * * * *